Figure 1:
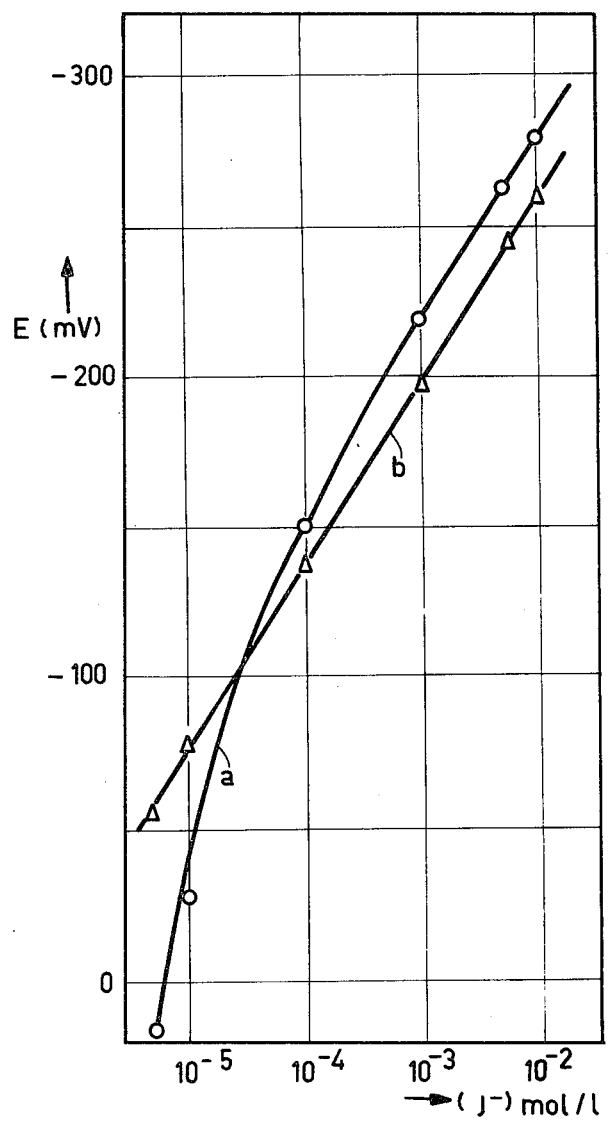

United States Patent [19]

van de Leest et al.

[11] 4,172,778

[45] Oct. 30, 1979

[54] ION-SELECTIVE ELECTRODE

[75] Inventors: Renaat E. van de Leest; Leopold Heijne, both of Eindhoven, Netherlands

[73] Assignee: U.S. Philips Corporation, New York, N.Y.

[21] Appl. No.: 960,368

[22] Filed: Nov. 13, 1978

Related U.S. Application Data

[63] Continuation of Ser. No. 787,973, Apr. 15, 1977, abandoned.

[30] Foreign Application Priority Data

Apr. 27, 1976 [NL] Netherlands .......................... 7604446

[51] Int. Cl.$^2$ ............................................. G01N 27/46
[52] U.S. Cl. ............................................... 204/195 M
[58] Field of Search .................. 204/195 M, 1 T, 1 B; 324/29

[56] References Cited

U.S. PATENT DOCUMENTS 3,563,874   2/1971   Ross et al. ........................ 204/195 M

FOREIGN PATENT DOCUMENTS 2519125   5/1976   Fed. Rep. of Germany ...... 204/195 M

OTHER PUBLICATIONS

J. H. Kennedy et al., J. Inorganic and Nuclear Chem., vol. 32, pp. 695-697, (1970).

Primary Examiner—G. L. Kaplan
Attorney, Agent, or Firm—Norman N. Spain

[57] ABSTRACT

Ion-selective electrode for determining the concentration of one specific ion in a solution of a mixture of different ions. The active material consists of $Ag_3SBr$ or $Ag_3SI$. The electrode is used for the selective determination of $Br^-$, $I^-$ or $Ag^+$.

4 Claims, 4 Drawing Figures

ION-SELECTIVE ELECTRODE

This is a continuation of application Ser. No. 787,973, filed Apr. 15, 1977 and now abandoned.

The invention relates to an ion-selective electrode and a method of making same.

U.S. Pat. No. 3,563,874 discloses an electrode for selectively measuring the concentration of a given ion in a mixture of different ions, which electrode comprises a nonporous membrane consisting of a mixture of silver sulfide and a silver halide. The halide may be chosen from silver iodide, silver bromide and silver chloride. Applicants ascertained that this electrode has a rather poor sensitivity and a slow response.

It is an object of the invention to provide an electrode having a high and reproduceable sensitivity and a rapid response, and, of course, a great specificity.

The electrode according to the invention is characterized in that its active material consists of $Ag_3SB_r$ or $Ag_3SI$ exclusively.

The above-mentioned United States Patent Specification describes an electrode of a mixture of $Ag_2S$ and AgBr or AgI and a method of making same. In this specification it is stated that after compressing the electrodes a considerable share of the compound $Ag_3SX$ (X=Br or I) is present in this electrode.

From the literature it is known that only after prolonged heating, for example for 4 weeks at 280° C. the mixture of the sulfide and halide is fully converted. Inter alia B. Reuter and K. Hardel in Z. Anorg u Allg. Chemie 340 158–167 (1965) and Yu. A. Shirokow c.s. in Elektrochimid 11 330–332 (1975) clearly ascertained this by means of X-ray diffraction experiments and by means of differential thermal analysis (DTA). DTA measurements give for the compounds $Ag_3SBr$ and $Ag_3SJ$ peaks at 430° C.±10° C. and 235°±10° C. respectively and, for example for a mixture of $Ag_2S+AgJ$ two peaks at 178° C. and at 147° C.

By simply compressing a mixture the relevant compounds cannot be formed, certainly not for a considerable part. Tests made by Applicants proved this unmistakably, also by means of DTA measurements and by X-ray diffraction but also by means of conductivity measurements. In the product obtained after compressing it was not possible to detect even a trace of the compounds.

A very advantageous method of making the electrode bodies according to the invention is that method in which the sulfide and the halide are coprecipitated, whereafter the precipitate is dried, heated, after-treated and compressed into a body. The method of preparing the starting material for the electrode body according to the invention is known per se from an article by J. H. Kennedy and F. Chen in J.Inorg.Nucl.Chem. 32 695 (1970). The dried precipitate was heated for 48 hours at 200° C. in an atmosphere containing sulphur vapour. In order to obtain usable electrodes a further after-treatment of the precipitate appeared to be necessary before the electrode bodies are compressed therefrom.

Without the after-treatment they show a concentration, depending on the EMK which does not proceed according to Nernst's law and a very low response.

For the production of electrode bodies of $Ag_3SI$ the after-treatment consists in that the precipitate is first exposed for a short time to the action of iodine vapour at room temperature.

When producing electrode bodies of $Ag_3SBr$ the after-treatment consists in that the electrode body or the precipitate are heated in contact with a coating of silver metal or kept into contact with a solution of a silver salt.

Another method of preparing $Ag_3SBr$ and $Ag_3SI$ is prolonged heating of a mixture of the sulfide and the halide (for example for 4 weeks) in an atmosphere containing sulphur vapour at a temperature exceeding 280° C. whilst occasionally grinding the product.

The electrodes according to the invention are suitable for selectively determining concentrations of silver ions, of bromide ions and of iodide ions. They are not suitable for the determination of sulfide ions.

The following embodiments serve to illustrate the invention.

1. From a solution which contains equimolar quantities of sodium sulfide and sodium iodide the mixture $Ag_2S+AgI$ was precipitated by means of a slight excess of silver nitrate. All three chemicals were of an analytical purity. The precipitate was filtered off, washed with demineralized water and thereafter heated for 48 hours at 200° C. in an atmosphere containing 0.07 torr sulphur vapour. After cooling the compounds formed were placed for one hour at room temperature in iodide vapour.

A quantity of, in all cases, 1 g of the product obtained was compressed at a pressure of 5000 kg/cm² together with a silver contact into electrode bodies having a diameter of 5 mm.

FIG. 1 (curve b) shows the variation in measurements of the EMF (E) in mV with respect to a saturated calomel reference electrode in a range of iodide concentrations. The curve varies according to Nernst's law with an E-slope of 58 mV/decade.

Figure 2:
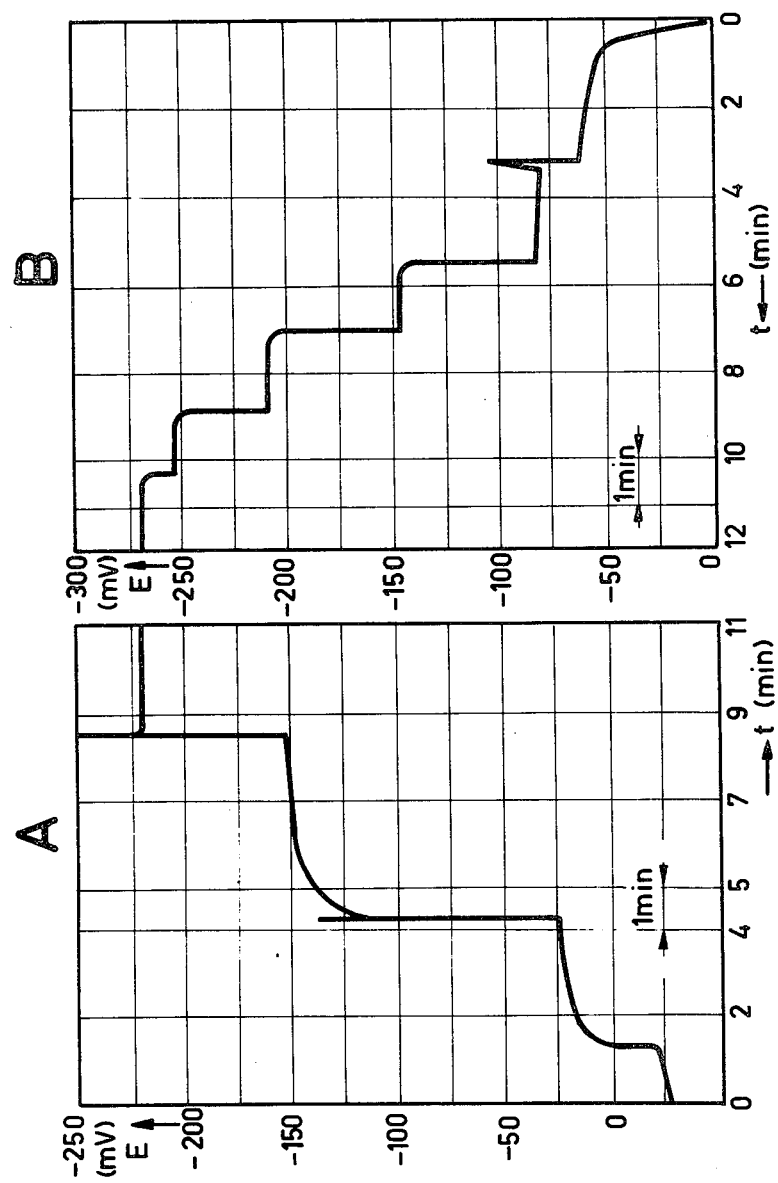

Curve (a) in FIG. 1 shows the behaviour of a non-aftertreated electrode for the purpose of comparison. Such an electrode is unsuitable, the more so as the response is very slow. This is illustrated in FIG. 2:

(A) is the E-t curve or a range of I-concentrations, measured with an electrode of non-aftertreated $Ag_3SI$ powder and (B) the curve where this has been done.

(2) A coprecipitate of $Ag_3SBr$ was made in an analogous manner as in Example 1. The filtered-off, washed and dried precipitate was heated for 48 hours at 200° C. in an atmosphere containing 0.07 torr of sulphur vapour. Thereafter the powder was placed for some minutes into contact with an 0.1 n $AgNO_3$-solution, thereafter washed and dried.

Each time 1 g of this powder was compressed at a pressure of 5000 kg/cm² together with a silver contact into electrode bodies having a diameter of 5 mm.

Figure 3:
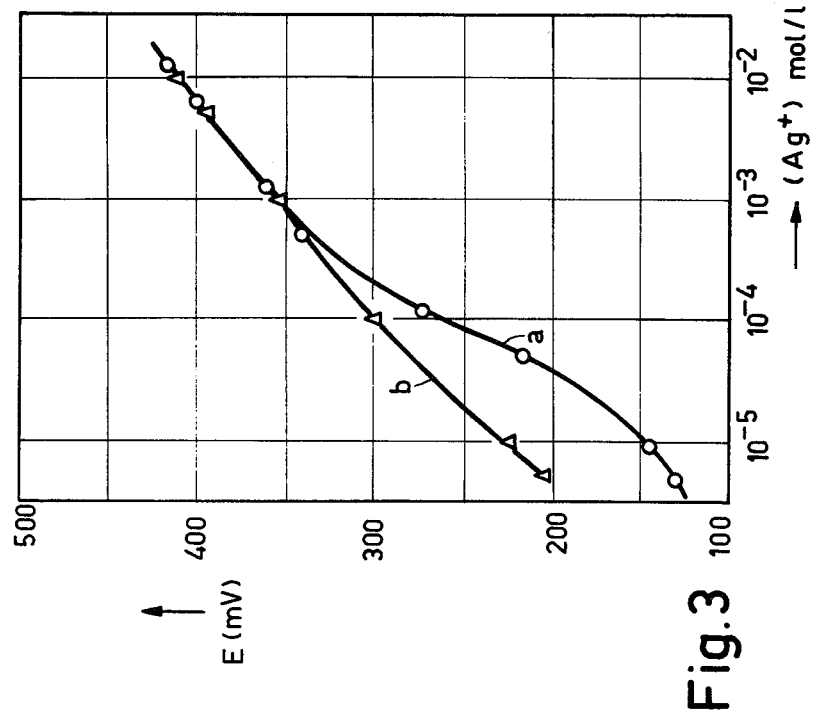

In FIG. 3 (curve b) is shown the variation of the EMF (E) in mV as a function of the ($Ag^+$) concentration with respect to a saturated calomel electrode, measured by means of a range of solutions having increasing $Ag^+$ concentrations. Curve a (in FIG. 3) shows the variation of E versus ($Ag^+$) when an electrode is used made of non-aftertreated $Ag_3SBr$ powder.

Figure 4:
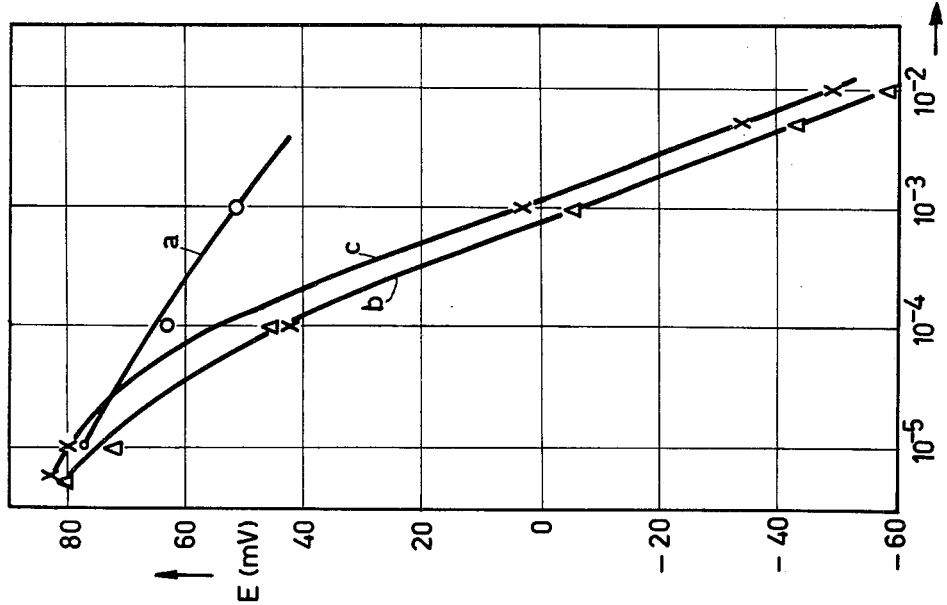

FIG. 4 shows the behaviour of the concentration measurements at bromide ions. Curves (b) and (c) apply to aftertreated $Ag_3SBr$ and follow Nernst's law in a large concentration range, whereas curve (a) applies to non-aftertreated $Ag_3SBr$.

Instead of aftertreating the $Ag_3SBr$ powder the $Ag_3SBr$ electrodes compressed with silver contacts may be heated for some hours at 60° C.

What is claimed is:

1. An ion-selective electrode for selectively determining the concentration of an iodide or bromide ion in a solution of a mixture of ions, said electrode comprising an ion-sensitive material selected from the group consisting of $Ag_3SBr$ and $Ag_3SI$ and mixtures thereof and an electrically conductive material, said $Ag_3SBr$ being heated in contact with a silver metal or a solution of a silver metal salt prior to being employed as an electrode and said $Ag_3SI$ being exposed to the action of iodine vapor at room temperature for a period of time prior to being employed as an electrode.

2. A method of producing an ion-selective electrode of claim 1 comprising coprecipitating silver sulfide and silver bromide, drying the resultant precipitate, heating the resultant dry precipitate in a sulfur containing atmosphere, heating the resultant $Ag_3SBr$ in contact with silver metal or with a solution of a silver salt and then compressing said thus treated $Ag_3SBr$, together with an electrically conductive material, into an electrode body.

3. A method of producing an ion-selective electrode of claim 1, said method comprising coprecipitating silver sulfide and silver iodide, drying the resultant precipitate, heating the resultant dry precipitate in an atmosphere containing sulfur vapor at a temperature of between 130° C. and 235° C., exposing the resultant $AG_3SI$ to the action of iodine vapor at room temperature and then compressing said thus treated $Ag_3SI$, together with an electrically conductive material, into an electrode body.

4. An assembly for selectively determining the concentration of silver ions, bromide ions or iodine ions in a mixture of ions, said assembly comprising an apparatus for measuring EMF, a reference electrode and an ion-selective electrode of claim 1, both of said electrodes being electrically connected to said EMF measuring apparatus.

* * * * *